United States Patent
Schindhelm et al.

(10) Patent No.: US 10,525,219 B2
(45) Date of Patent: Jan. 7, 2020

(54) METHODS AND APPARATUS FOR MONITORING AND TREATING RESPIRATORY INSUFFICIENCY

(71) Applicant: ResMed Sensor Technologies Limited, Clonskeagh, Dublin (IE)

(72) Inventors: Klaus Henry Schindhelm, Glenhaven (AU); Steven Paul Farrugia, Lugarno (AU)

(73) Assignee: ResMed Sensor Technologies Limited (IE)

( * ) Notice: Subject to any disclaimer, the term of this patent is extended or adjusted under 35 U.S.C. 154(b) by 560 days.

(21) Appl. No.: 13/907,099

(22) Filed: May 31, 2013

(65) Prior Publication Data
US 2013/0340758 A1    Dec. 26, 2013

(30) Foreign Application Priority Data
Jun. 26, 2012   (AU) .................................. 2012902693

(51) Int. Cl.
*A61M 16/00*    (2006.01)
(52) U.S. Cl.
CPC ................ *A61M 16/0051* (2013.01)
(58) Field of Classification Search
None
See application file for complete search history.

(56) References Cited

U.S. PATENT DOCUMENTS

| 4,944,310 A | 7/1990 | Sullivan |
| 5,704,345 A | 1/1998 | Berthon-Jones |
| 5,738,102 A * | 4/1998 | Lemelson ............ A61B 5/0205 |
| | | 128/903 |

(Continued)

FOREIGN PATENT DOCUMENTS

| CN | 101489478 A | 7/2009 |
| DE | 102007039004 A1 | 3/2008 |

(Continued)

OTHER PUBLICATIONS

Senske, A View Inside a Respironics REMstar Pro CPAP Machine (https://www.cpap-supply.com/Articles.asp?ID=134) (Last Updated Jan. 5, 2007 3:56:00 PM). (Year: 2007).*

(Continued)

*Primary Examiner* — Peter S Vasat
(74) *Attorney, Agent, or Firm* — Botos Churchill IP Law LLP

(57) ABSTRACT

An apparatus, such as a pressure support ventilator or respiratory monitor, provides operations for a patient, such as a patient with heart failure, Chronic Obstructive Pulmonary Disease or other respiratory insufficiency. In some embodiments, the apparatus may detect a respiratory condition, such as a decompensation event and/or exacerbation event, from respiratory parameters. A clinical alert message may be transmitted or displayed for a physician based on the results of query presented to the patient in response to an analysis of the one or more respiratory parameters. In some embodiments, the apparatus generates a potential relapse indicator that may provide a prediction of a risk of an oncoming clinical event such as for evaluating whether to release the patient from a hospital.

36 Claims, 4 Drawing Sheets

(56) References Cited

U.S. PATENT DOCUMENTS

| | | | |
|---|---|---|---|
| 6,367,475 B1* | 4/2002 | Kofoed | A61B 5/087 |
| | | | 128/200.24 |
| 6,390,091 B1 | 5/2002 | Banner et al. | |
| 6,532,957 B2 | 3/2003 | Berthon-Jones | |
| 6,532,959 B1 | 3/2003 | Berthon-Jones | |
| 6,600,949 B1* | 7/2003 | Turcott | A61B 5/0002 |
| | | | 600/481 |
| 6,635,021 B1 | 10/2003 | Sullivan et al. | |
| 6,845,773 B2 | 1/2005 | Berthon-Jones et al. | |
| 6,895,963 B1* | 5/2005 | Martin et al. | 128/204.21 |
| 6,951,217 B2 | 10/2005 | Berthon-Jones | |
| 7,551,078 B2 | 6/2009 | Carlson et al. | |
| 7,593,952 B2* | 9/2009 | Soll et al. | |
| 8,844,525 B2 | 9/2014 | Schindhelm et al. | |
| 2004/0122487 A1* | 6/2004 | Hatlestad et al. | 607/60 |
| 2004/0236240 A1 | 11/2004 | Kraus et al. | |
| 2005/0076615 A1 | 4/2005 | Wallis | |
| 2007/0118054 A1 | 5/2007 | Pinhas et al. | |
| 2007/0161913 A1* | 7/2007 | Farrell et al. | 600/484 |
| 2007/0213622 A1 | 9/2007 | Reisfeld | |
| 2007/0215146 A1* | 9/2007 | Douglas et al. | 128/200.24 |
| 2007/0293779 A1 | 12/2007 | Bardy | |
| 2008/0000475 A1 | 1/2008 | Hill | |
| 2008/0004906 A1 | 1/2008 | Klass et al. | |
| 2008/0053440 A1* | 3/2008 | Farrugia | 128/204.23 |
| 2008/0177195 A1 | 7/2008 | Armitstead | |
| 2008/0275349 A1 | 11/2008 | Halperin et al. | |
| 2009/0121854 A1 | 5/2009 | Raisanen et al. | |
| 2009/0131803 A1 | 5/2009 | Heneghan et al. | |
| 2009/0149778 A1* | 6/2009 | Naujokat | A61B 5/0002 |
| | | | 600/595 |
| 2009/0203972 A1 | 8/2009 | Heneghan et al. | |
| 2009/0314290 A1 | 12/2009 | Hickle | |
| 2010/0018530 A1 | 1/2010 | Schindhelm et al. | |
| 2010/0022911 A1 | 1/2010 | Wariar et al. | |
| 2010/0204550 A1 | 8/2010 | Heneghan et al. | |
| 2010/0258124 A1 | 10/2010 | Madaus et al. | |
| 2010/0275921 A1* | 11/2010 | Schindhelm | A61B 5/08 |
| | | | 128/204.23 |
| 2011/0178377 A1 | 7/2011 | Heneghan et al. | |
| 2011/0179361 A1* | 7/2011 | Cardarelli et al. | 715/744 |
| 2011/0224517 A1 | 9/2011 | Lvarez Gonz Lez et al. | |
| 2011/0263997 A1 | 10/2011 | Corn | |
| 2012/0116202 A1* | 5/2012 | Bangera | A61B 5/0507 |
| | | | 600/407 |
| 2012/0138533 A1* | 6/2012 | Curtis et al. | 210/646 |
| 2012/0145153 A1* | 6/2012 | Bassin | A61M 16/024 |
| | | | 128/204.23 |
| 2013/0165807 A1* | 6/2013 | Gobbi | A61B 5/085 |
| | | | 600/533 |

FOREIGN PATENT DOCUMENTS

| | | |
|---|---|---|
| JP | 2009532072 A | 9/2009 |
| JP | 2009538720 A | 11/2009 |
| NZ | 552070 A | 11/2008 |
| WO | 96/32055 A1 | 10/1996 |
| WO | 98/52467 A1 | 11/1998 |
| WO | 2004013611 A2 | 2/2004 |
| WO | 2006-037184 A1 | 4/2006 |
| WO | 2006066337 A1 | 6/2006 |
| WO | 2007124126 A2 | 11/2007 |
| WO | 2007143535 A2 | 12/2007 |
| WO | 2009026582 A1 | 2/2009 |
| WO | 2007052108 A3 | 4/2009 |
| WO | 2009136337 A1 | 11/2009 |
| WO | 2011141916 A1 | 11/2011 |
| WO | WO 2012032402 A1 * 3/2012 ............. A61B 5/085 |

OTHER PUBLICATIONS

Vasilliou et al. in "Expiratory flow limitation during mechanical ventilation detected by the forced oscillation method", Eur Respir J, 1996, 9, 779-786.

Peslin et al. in "Respiratory mechanics studied by forced oscillations during artificial ventilation", Eur Rospir J, 1993, 6, 772-784.

Dai Yumino and T. Douglas Bradley "Central Sleep Apnea and Cheyne-Stokes Respiration", Proceedings of the American Thoracic Society, vol. 5, No. 2 (2008), pp. 226-236.

White et al., "Role of nocturnal rostral fluid shift in the pathogenesis of obstructive and central sleep apnoea", J Physiol., Mar. 1, 2013, 591, pp. 1179-1193.

International Search Report for Application No. PCT/AU2013/000564 dated Aug. 29, 2013.

Extended European Search Report for Application No. 13796432.6 dated Jan. 21, 2016.

First Examination Report issued in corresponding AU application No. 2017200083 dated Jun. 28, 2018.

* cited by examiner

METHODS AND APPARATUS FOR MONITORING AND TREATING RESPIRATORY INSUFFICIENCY

CROSS-REFERENCE TO RELATED APPLICATIONS

This application claims the benefit of Australia provisional application no. AU 2012902693, filed Jun. 26, 2012, the disclosure of which is incorporated herein in its entirety by reference.

FIELD OF THE TECHNOLOGY

The present technology relates to systems, methods and apparatus for detecting respiratory conditions and/or treating heart failure patients or others with respiratory insufficiency such as Chronic Obstructive Pulmonary Disease.

BACKGROUND OF THE TECHNOLOGY

Respiratory insufficiency affects millions of people, including heart failure patients. For patients suffering from this condition, the lungs are unable to inspire sufficient oxygen or expel sufficient carbon dioxide to meet the needs of the cells of the patient's body. This will typically manifest itself in some difficulty with breathing such as dyspnea.

For example, Chronic Obstructive Pulmonary Disease ("COPD") affects approximately thirteen million Americans and ten million Europeans. COPD is a disease involving some damage to the lungs. The airways and the alveoli of the lungs can lose their elastic quality. Walls between alveoli can become destroyed or they can become inflamed. The airways of the lungs may also produce more mucus than usual, which can restrict airflow. COPD patients typically experience coughing, with an expulsion of mucus, shortness of breath, wheezing and a feeling of tightness in the chest. Emphysema and chronic obstructive bronchitis may each be considered to be a form of COPD. Chronic obstructive bronchitis may be characterized by an inflammatory response in the larger airways of the lungs. Emphysema may be characterized by destruction of tissue of the lungs from an inflammatory response.

Respiratory insufficiency can cause patients to have difficulty with performing physical activities such as walking or exercise. In some situations, a patient suffering from heart failure or COPD may experience decompensations and/or exacerbations that may lead to acute hospitalization.

It will be appreciated that there is a need in the art for improved techniques and devices for addressing the conditions of patients suffering from respiratory insufficiency or COPD.

SUMMARY OF THE TECHNOLOGY

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

Some embodiments of the present technology involve an apparatus for monitoring a patient's respiratory parameters such as with patient suffering from respiratory insufficiency.

Some embodiments of the technology involve an apparatus for predicting changes to such patient's condition.

Some embodiments of the technology involve an apparatus for providing a pressure treatment, such as a pressure support ventilation treatment to promote patient mobility.

Some embodiments of the technology may include an apparatus for evaluating sensor signals representative of respiratory characteristics. The apparatus may include at least one sensor adapted to measure at least one respiratory parameter of the patient, a display, and a controller. The controller may be coupled to the at least one sensor and the display. The controller may also be configured to (i) evaluate the at least one respiratory parameter, (ii) generate a presentation of at least one query on the display based on the evaluation, the query being configured to prompt for an input to the controller, and (iii) generate an alert message based on a user response to the query that is input to the controller. The controller may include a memory with a data structure of questions, each question associated with a detectable condition of the at least one respiratory parameter. In some cases, one or more of the questions may address either or both of medication compliance and dietary compliance.

In an example, the controller may be further configured to select a first question in response to a detected condition of the respiratory parameter, and based on an input response to the first question, continue to evaluate the at least one respiratory parameter in a subsequent monitoring session before generating an alert message. In some cases, the controller may be further configured to generate the alert message following the subsequent monitoring session and the generation of the alert message is based on a user response to a second question presented by the controller.

Optionally, the apparatus may include a flow generator configured to generate a flow of breathable gas at a pressure above atmospheric pressure to a patient interface. In such a case, the controller may be configured to control the flow generator. The controller may also be configured to modify a pressure control parameter of the flow generator based on the at least one query. Such a control parameter may include a target ventilation.

In some embodiments, the alert message may include a warning presented on the display. The apparatus may also include a communications device and the alert message may include an electronic message transmitted from the communications device.

In some examples of the apparatus, the evaluation of the at least one respiratory parameter may include a detection of dyspnoea.

Some embodiments of the present technology may also involve a method of an apparatus for evaluating sensor signals representative of respiratory characteristics. The method of the apparatus may include evaluating at least one respiratory parameter from a sensor signal with a processor. The method of the apparatus may also include. The method of the apparatus may also include generating with the processor a presentation of at least one query on a display based on the evaluation where the query may be configured to prompt for an input to the controller. The method of the apparatus may also include generating an alert message with the processor based on a user response to the query that is input to the controller.

In some cases, the method may further include accessing in a memory, a data structure of questions. Each such question may be associated with a detectable condition of the at least one respiratory parameter. For example, a question may address medication compliance. A question may also address dietary compliance. The method may further include selecting with the processor a first question in response to a detected condition of the respiratory parameter, and based on an input response to the first question, continuing to evaluate the at least one respiratory parameter in a subsequent monitoring session before generating an alert message. In such methods, the processor may generate the alert message following the subsequent monitoring session and the generation of the alert message may be based on a user response to a second question presented by the processor on the display.

In some embodiments, the method may further include generating, with the processor and a flow generator, a flow of breathable gas at a pressure above atmospheric pressure to a patient interface during the evaluating. In some such cases, the method may also include modifying a pressure control parameter for the flow of breathable gas based on the at least one query. The control parameter may include a target ventilation. The method may further include presenting the alert message on the display. In some cases, the method may also include transmitting, with a communications device, the alert message as an electronic message to another apparatus. Furthermore, the evaluating of the at least one respiratory parameter may include detecting dyspnoea.

Some embodiments of the present technology may involve an apparatus for evaluating sensor signals representative of respiratory characteristics. The apparatus may include at least one sensor adapted to measure at least one respiratory parameter. The apparatus may also include a controller. The controller may be coupled to the at least one sensor. The controller may also be configured to (i) evaluate the at least one respiratory parameter during one or more monitoring sessions and (ii) generate for display a potential relapse indicator based on the evaluation of the at least one respiratory parameter. In some cases, the evaluation of the at least one respiratory parameter may include evaluation of a detected respiratory rate. In some cases, evaluation of the at least one respiratory parameter may include an evaluation of sleep disordered breathing events. The evaluation of the at least one respiratory parameter may include evaluation of a measure of ventilation. The evaluation of the at least one respiratory parameter may include evaluation of a change in the at least one respiratory parameter over the one or more monitoring sessions.

Optionally, the potential relapse indicator may comprise a numerical value and/or a calculated probability. In some cases, the generation of the potential relapse indicator may include a comparison of changes in a plurality of respiratory parameters with a plurality of thresholds. Also, the controller may be further configured to display the potential relapse indicator on a display. Furthermore, the apparatus may further include a flow generator configured to generate a flow of breathable gas at a pressure above atmospheric pressure to a patient interface, wherein the controller is configured to control the flow generator.

Some embodiments of the present technology may involve a method for evaluating sensor signals representative of respiratory characteristics. The method may include measuring at least one respiratory parameter with at least one sensor. The method may also include evaluating with a processor the at least one respiratory parameter during one or more monitoring sessions The method may also include generating for display with the processor a potential relapse indicator based on the evaluation of the at least one respiratory parameter. The evaluating of the at least one respiratory parameter may include evaluation of a detected respiratory rate, evaluation of sleep disordered breathing events, evaluation of a measure of ventilation, and/or evaluation of a change in the at least one respiratory parameter over the one or more monitoring sessions. In some case, the potential relapse indicator may include a numerical value and/or a calculated probability. Moreover, the generating of the potential relapse indicator may include a comparison of changes in a plurality of respiratory parameters with a plurality of thresholds. The generating for display may present the potential relapse indicator on a display. The method may further include generating a flow of breathable gas at a pressure above atmospheric pressure to a patient interface with a flow generator under of the processor.

Some embodiments of the present technology involve an apparatus to generate pressure support ventilation. The apparatus may include at least one sensor adapted to measure at least one respiratory parameter and a flow generator adapted for coupling with a patient respiratory interface. The flow generator may be configured to provide a flow of breathable gas for pressure support ventilation to the patient respiratory interface. The apparatus may also include a controller coupled to the at least one sensor and the flow generator. The controller may be configured to control the pressure support ventilation with the flow generator. The controller may also be further configured with a rest mode and an exercise mode, the rest mode having a first value set of control parameters for the pressure support ventilation and the exercise mode having a second value set of control parameters for the pressure support ventilation.

In some cases, the controller may be configured to receive a user activated trigger stimulus, and, in response to the trigger stimulus to select the second value set of control parameters for the exercise mode. In response to the trigger stimulus, the controller may set a target respiratory control parameter as a function of a presently detected respiratory parameter sensed with the sensor. The target respiratory control parameter may be a target respiratory rate and the detected respiratory parameter may be a measured respiratory rate. The target respiratory control parameter may be a target ventilation and the detected respiratory parameter may be a measure of ventilation. Optionally, the target ventilation may be a target tidal volume and the measure of ventilation may be a measure of tidal volume. Still further, the target ventilation may be a target minute ventilation and the measure of ventilation may be a measure of minute ventilation. In some cases, the second value set of control parameters may comprise an increase in target values with respect to the first value set of control parameters.

Optionally, the apparatus may further include at least one user accessible button to activate the controller such that the button may be configured for actuating the trigger stimulus. Still further, the apparatus may also include a diaphragm electromyogram sensor to activate the controller such that the sensor may be configured for actuating the trigger stimulus. In some cases, the apparatus may include a vagal nerve sensor to activate the controller such that the sensor may be configured for actuating the trigger stimulus.

In some cases, the controller of the apparatus may be further configured with a cool down mode, and configured to receive another user activated trigger stimulus to initiate the cool down mode. The cool down mode may include a third value set of control parameters for the pressure support ventilation. The controller may be configured such that a value of the control parameters of the cool down mode may be varied from a respective value of the control parameters of the exercise mode toward a respective value of the control parameters of the rest mode. The controller may be configured such that a value of the control parameters of the cool down mode may be ramped from a respective value of the control parameters of the exercise mode toward a respective value of the control parameters of the rest mode.

Some embodiments of the present technology may involve a method for control of pressure support ventilation. The method may include measuring at least one respiratory parameter with a sensor. It may also include generating pressure support ventilation with a flow generator adapted for coupling with a patient respiratory interface. It may further include controlling, with a processor, the pressure support ventilation in a rest mode and an exercise mode. The rest mode may have a first value set of control parameters for controlling the pressure support ventilation and the exercise mode may have a second value set of control parameters for controlling the pressure support ventilation.

The method may further include receiving a user activated trigger stimulus, and, in response to the trigger stimulus, selecting the second value set of control parameters for the exercise mode. The method may also include, in response to the trigger stimulus, setting a target respiratory control parameter as a function of a presently detected respiratory parameter sensed with the sensor. The target respiratory control parameter may be a target respiratory rate and the detected respiratory parameter may be a measured respiratory rate. The target respiratory control parameter may be a target ventilation and the detected respiratory parameter may be a measure of ventilation. The target ventilation may be a target tidal volume and the measure of ventilation may be a measure of tidal volume. The target ventilation may be a target minute ventilation and the measure of ventilation may be a measure of minute ventilation. The second set of control parameters may include an increase in target values with respect to the first value set of control parameters. In some such methods, a user accessible button actuates the trigger stimulus. In some such methods, a diaphragm electromyogram sensor actuates the trigger stimulus. Still further, in some such methods, a vagal nerve sensor actuates the trigger stimulus.

Optionally, the methods may also include controlling pressure support ventilation in a cool down mode in response to receiving another user activated trigger stimulus, the cool down mode may have a third value set of control parameters for the pressure support ventilation. In some cases, a value of the control parameters of the cool down mode may be varied from a respective value of the control parameters of the exercise mode toward a respective value of the control parameters of the rest mode. In some cases, a value of the control parameters of the cool down mode may be ramped from a respective value of the control parameters of the exercise mode toward a respective value of the control parameters of the rest mode.

Various aspects of the described example embodiments may be combined with aspects of certain other example embodiments to realize yet further embodiments.

Other features of the technology will be apparent from consideration of the information contained in the following detailed description, abstract and claims.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION

The present technology involves methods and devices for patients with respiratory insufficiency (RI) such as heart failure patients or patients with chronic obstructive pulmonary disease (COPD). The technology may be implemented to monitor and/or treat the condition of such patients before, during and after hospitalization. For example, heart failure and COPD patients may suffer from exacerbation or decompensation events. These events may require modifications to medical treatment. Untreated exacerbation could lead to further exacerbation and potentially require hospitalization for the patient. However, if exacerbation is discovered early enough, such as at the earliest stages of its onset, it may be treated in a manner that may avoid hospitalization.

Figure 1:
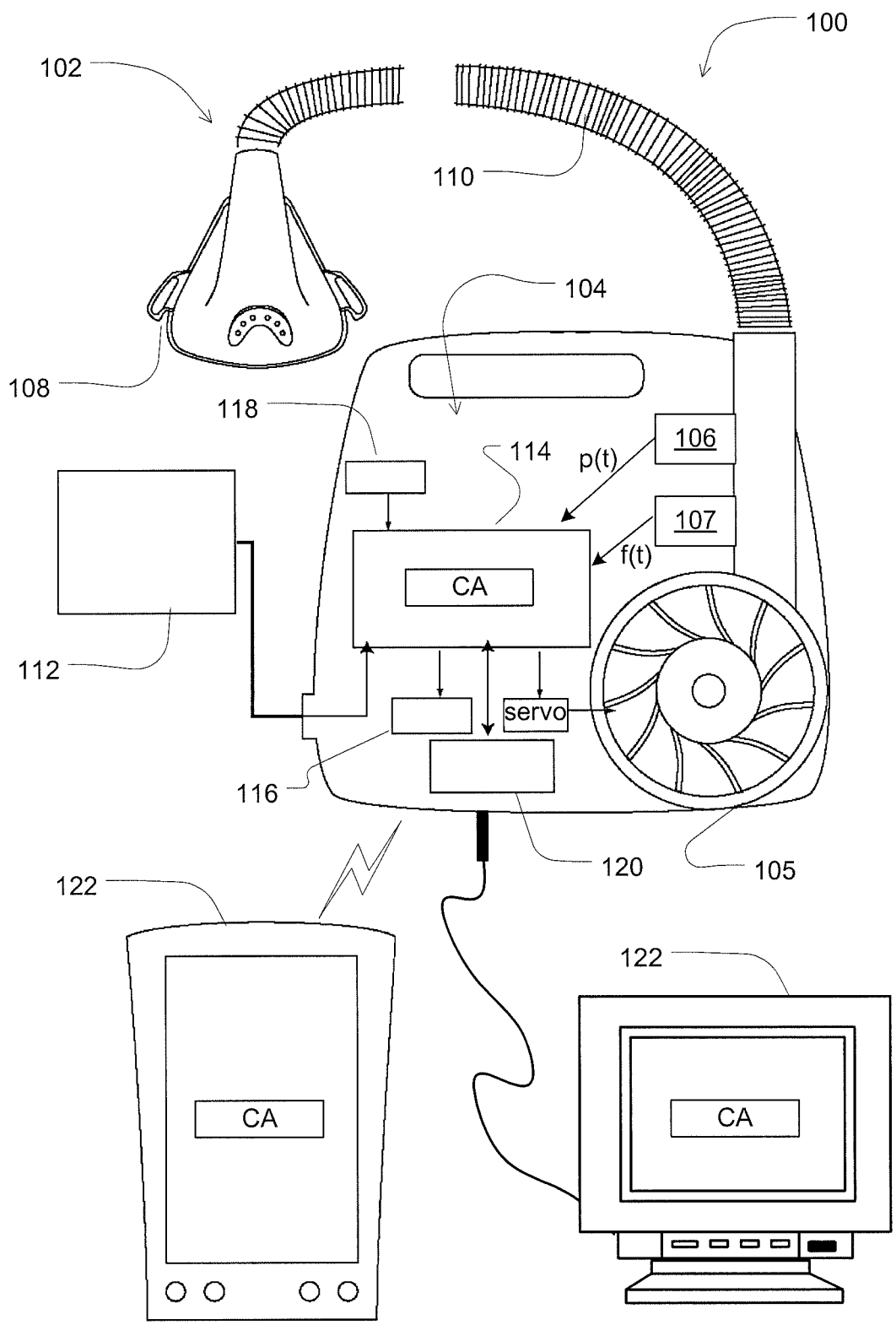
FIG. 1 illustrates example components of a monitoring apparatus for monitoring, predicting and/or treating a respiratory insufficiency or chronic obstructive pulmonary disease patient.

An example embodiment of a device for implementing one or more of the methods of the present technology is illustrated in FIG. 1. In the embodiment, the monitoring apparatus 100 may implement a RI or COPD clinical alert (referenced in FIG. 1 as "CA"). In some embodiments, the monitoring apparatus 100 may include a patient respiratory interface 102, a delivery tube 110, a controller 104 and a flow generator such as a servo-controlled blower 105.

The patient respiratory interface such as a mask 108 as shown together with the delivery tube 110, provides a respiratory treatment to the patient's respiratory system via the patient's mouth and/or the patient's nares. Optionally, the patient respiratory interface may be implemented with a nasal mask, nose & mouth mask, full-face mask or nasal pillows or tracheostomy tube.

With the flow generator, the monitoring apparatus 100 can be configured to generate a respiratory pressure treatment at the patient respiratory interface. To assist this end, the device may further include a pressure sensor 106, such as a pressure transducer to measure the pressure generated by the blower 105 and generate a pressure signal p(t) indicative of the measurements of pressure. In such a device, the delivery tube 110 may serve as the sense tube to permit detection of pressure levels supplied to the mask or patient respiratory interface.

The monitoring apparatus 100 may also optionally be equipped with a flow sensor 107, which may be coupled with the patient respiratory interface. The flow sensor generates a signal representative of the patient's respiratory flow. The signals from the sensors may be used to detect obstructive or central apneas, hypopneas, cardiogenic airflow, respiratory rates and other respiratory related parameters from the signals measured by the sensors as discussed in more detail herein. In some embodiments, flow proximate to the mask 108 or delivery tube 110 may be measured using a pneumotachograph and differential pressure transducer or similar device such as one employing a bundle of tubes or ducts to derive a flow signal f(t). Alternatively, a pressure sensor may be implemented as a flow sensor and a flow signal may be generated based on the changes in pressure.

Although the pressure or flow sensors are illustrated in a housing of the controller 104, they may optionally be located closer to the patient, such as in the mask 108 or delivery tube 110. Other devices for generating a respiratory flow signal or pressure signal may also be implemented. For example, a motor RPM sensor may be utilized to estimate pressure or flow information supplied by the flow generator device based upon the characteristics of the system.

Based on flow f(t) and/or pressure p(t) signals, the controller 104 with one or more processors 114 generates blower control signals. For example, the controller may generate a desired pressure set point and servo-control the blower to meet the set point by comparing the set point with the measured condition of the pressure sensor. Thus, the controller 104 may make controlled changes to the pressure delivered to the patient interface by the blower. Optionally, such changes to pressure may be implemented by controlling an exhaust with a mechanical release valve (not shown) to increase or decrease the exhaust while maintaining a relatively constant blower speed.

With such a controller or processor, the apparatus can be used for many different pressure treatment therapies, such as the pressure treatments for sleep disordered breathing, Cheyne-Stokes Respiration, obstructive sleep apnea (e.g., CPAP, APAP, Bi-Level CPAP, AutoVPAP), etc., or combinations thereof by adjusting a suitable pressure delivery equation. For example, the pressure treatment therapies of the devices described in U.S. Pat. Nos. 6,532,957, 6,845,773 and 6,951,217, which are incorporated herein by reference in their entireties, may be implemented with a monitoring apparatus 100 of the present technology. For example, as described in these patents, the controller and flow generator may be configured to provide pressure support ventilation. Such a treatment may ensure delivery of a specified or substantially specified target ventilation, for example, a minute ventilation, a gross alveolar ventilation or a alveolar ventilation, to the patient interface during the course of a treatment session by comparing an measure of ventilation with the target ventilation; or delivery of a tidal volume by comparing a measure of tidal volume with a target tidal volume. Thus, if a patient's respiration causes the measured ventilation to fall below or rise above the target ventilation over time, the flow generator will compensate with an increase or decrease respectively in the supplied pressure support ventilation. This may be accomplished with pressure variations that provide a bi-level form of therapy or some other form of therapy that may more smoothly replicate changes in a patient's respiration cycle. While the embodiment of FIG. 1 illustrates a flow generator for generating such pressure support ventilation, as described herein, in some cases a monitoring apparatus may be implemented for monitoring without a flow generator for a pressure treatment.

Optionally, the monitoring apparatus 100 may also include additional diagnosis sensors 112 that may be contact or non-contact sensors. For example, the device may include an oximeter. The oximeter may generate a signal representative of a blood oxygen level of a patient. A suitable example oximeter or monitor device may optionally be any of the devices disclosed in International Patent Application No. International Application No. PCT/AU2005/001543 (Pub. No. WO/2006/037184) or International Patent Application No. PCT/AU1996/000218 (Pub. No. WO/1996/032055), the disclosures of which are incorporated herein by cross-reference. As disclosed in these incorporated PCT applications, the monitor may serve as diagnosis sensors that can also optionally provide a blood pressure and/or heart or pulse rate monitor for measuring a heart rate and/or blood pressure of the patient.

In some embodiments, the diagnosis sensors may also include an ECG monitor. Such a device may be configured to detect cardiac-related characteristics such as a heart rate and may also determine respiratory parameters (such as central or obstructive apneas, hypopneas, etc.) Optionally, these parameters may be determined by the analysis algorithms of controller 104 based on transmission of the ECG data to the controller or they may be determined by the monitor and be transmitted to the controller 104.

In some embodiments, the diagnosis sensors may include a movement sensor. For example, a suprasternal notch sensor or chest band may be implemented to generate a movement signal that is indicative of patient effort during respiration. Other suitable sensors may include the movement sensing devices disclosed in International Patent Application No. PCT/AU1998/000358 (Pub. No. WO1998/052467), the disclosure of which is incorporated herein by cross-reference. The movement sensors thus may provide a measure of patient effort and/or respiration rate and may be used as an alternative to a flow sensor or in conjunction with other flow sensors as discussed in more detail herein.

Some embodiments may monitor respiratory parameters with non-contact infrared or wireless biomotion sensors. One such example is the BiancaMed Doppler device which uses low power pulses of radio frequency energy transmitted and reflected back to a sensor to detect respiration rate, heart rate and movement, etc. Alternatively, or in addition thereto, contact respiratory monitoring devices such as a respiratory band or movement sensitive bed may be implemented to monitor patient respiratory parameters.

The signals from the sensors may be sent to the controller 104. Optional analog-to-digital (A/D) converters/samplers (not shown separately) may be utilized in the event that supplied signals from the sensors are not in digital form and the controller is a digital controller. Based on the signals from the sensor(s), the controller assesses the condition of the patient.

The controller may optionally include a display device 116 such as one or more warning lights (e.g., one or more light emitting diodes). The display device may also be implemented as a display screen such as an LCD or a touch sensitive display. Activation of the display device 116 will typically be set by the controller based on an assessment of the condition by the monitoring apparatus 100. The display device may be implemented to visually show information to a user of the monitoring apparatus 100 or a clinician or physician. The display device 116 may also show a graphic user interface for operation of the monitoring apparatus 100. User, clinician or physician control of the operation of the monitoring apparatus 100 may be based on operation of input switches 118 that may be sensed by the controller or processor of the monitoring apparatus.

Optionally, the controller may also include a communications device 120 for receiving and/or transmitting data or messages by the monitoring apparatus 100. For example, the communications device may be a wireless transceiver such as Bluetooth or WIFI transceiver. The communications device may also be a network communications device such as a phone modem and/or network card and may be implemented to send messages via the internet directly or through a computer to which the detection device may be docked. In general, the communications device 120 may be used to transmit alerts or messages to a clinician or physician accessible apparatus 122 such as a multi-patient monitoring system that allows a physician to review data from remote patient data recording devices such as the monitoring apparatus 100. In these systems, a database may be provided to record patient monitoring data. Physicians or clinicians may receive a report or warning that the patient may require closer observation or should be brought to hospital.

The controller 104 or processor 114 will typically be configured to implement one or more particular control methodologies such as the algorithms described in more detail herein. Thus, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium. With such a controller or processor, the device can determine and analyze many different parameters associated with the patient's condition based on data from the sensors, such as, for predicting a potential for a discharged hospital patient's re-admission. In some embodiments, patient queries may be triggered in response to such determinations or assessments to regulate a subsequent generation or transmission of alert messages based on responses to the queries. In still further embodiments, control over parameters of treatment may be set in accordance with a patient synchronization demand so as to permit a suitable treatment for mobility or exercise.

(1) Alerts Based on a Generated Patient Query

In at least some embodiments, a processor or controller of a monitoring apparatus, such as a respiratory treatment device, is configured to evaluate respiratory related data, such as to detect a patient's condition or changes to a patient's condition. The processed data may be derived from sensor signals from one or more of the previously described sensors. The processed data may be evaluated to trigger an alert message based on a detection of some pattern of the signals. Examples of such evaluations, which may include evaluation of one or more change condition indicators, are described in U.S. patent application Ser. No. 12/751,174, filed on Mar. 31, 2010 and U.S. patent application Ser. No. 12/483,357, filed on Jun. 12, 2009, the entire disclosures of which are incorporated herein by cross reference. However, in some cases the determination of the processor may condition an alert message on input responses to a triggered patient query that may serve to avoid unnecessary alerts. For example, based on an evaluation of data by the monitoring apparatus (e.g., a comparison of one or more respiratory parameters or indicators with one or more thresholds) the processor may trigger a presentation of a patient query to the patient to prompt the patient for input based on the assessment made by the processor. In such a case, the display device 116 under control of the processor may present a query to the patient, prompting the patient to input additional information. The presented question or questions of the query may be selected from a database, or other data structure of questions, such as a data structure in a memory of the apparatus, such that the selected ones are particularly associated with a pattern detected by the processor. The processor may then further evaluate data of the responses received in response to the query through a user interface associated with the monitoring apparatus. Based on this further evaluation, the processor may trigger an alert message, refrain from triggering an alert message and/or delay a triggering of an alert message pending responses to one or more additional triggered queries. Such additional queries may be triggered after a certain time, after a further detected pattern or after a further use of the monitoring apparatus.

For example, when monitoring a heart failure patient for imminent acute decompensated heart failure (ADHF) events and/or COPD patients for exacerbations, it may be desirable to query the patient to qualify a pattern detection made by the monitoring apparatus. Such queries may serve to reduce false positives (e.g., when an algorithm of the processor predicts a need for clinical contact and the clinical contact is later found to have been unnecessary). This type of false positive may be due to changes in patient behavior, which may be corrected without medical intervention. Such behaviors may include missed or incorrect dosage of medication, non-compliance of dietary instructions and/or rest requirements and the like.

For example, in some embodiments, in an effort to minimize false positives, a methodology of the processor may detect a respiratory pattern or events that might require a clinical alert (e.g., a certain number of respiratory events over a certain period of time that may be indicative of COPD and/or heart failure exacerbation or decompensation). Based on the detected pattern or events, the processor may present one or more questions in a query to the patient on a user interface of the apparatus. Such questions may address pharmaceutical and/or lifestyle compliance by the patient (e.g., has the patient been taking prescribed medication and/or following physician's treatment advice, etc.). Optionally, in some cases, one or more questions may address the operational integrity of the monitoring apparatus to ensure that the collected data is valid. Optionally, the processor may perform a series of inquiries over a predetermined span of time (such as one or more monitoring sessions or nights of sleep) and initiate a clinical alert only after the predetermined span of time has elapsed.

For example, if a recurring respiratory pattern (such as one repeatedly detected in several monitoring sessions) indicates a likelihood of a significant event, the processor may prompt a series of queries to the patient regarding diet that might have a causal relationship with the recurring pattern. If the patient is not in compliance with the dietary requirements as determined by the patient's responses input to the processor, the processor may then continue to monitor and query the patient again after a further monitoring time period has elapsed (e.g., query the patient after a number of minutes, hours, or days). If the processor detects a continuation of the detected respiratory pattern and the patient's responses indicate that diet is not a cause (e.g., the patient responds to a subsequent query that he or she is now in compliance with the dietary requirements), the processor may then trigger a clinical alert message to a clinician via a notification infrastructure (e.g., tele-monitoring) to notify a clinician directly as described below. In some cases, a certain received response(s) to one or more questions of the query may alternatively rule out the triggering of such an alert message. For example, a query and response may determine that the patient was not wearing his or her mask and as a result, the processor may refrain from triggering an alert.

The technology described above may be further illustrated with the following example: A heart failure patient does not take the prescribed diuretics for a period of time. Due to noncompliance, the patient experiences dyspnoea and breathing irregularities at night. The processor of the monitoring device may detect such events, or a pattern of such an events, that may be indicative of an imminent decompensation or exacerbation. Instead of directly issuing a clinical alert to the physician, the monitoring device may trigger a query to the patient (e.g., via display device 116) to determine whether the patient has taken the prescribed diuretics. The evaluation of the response may trigger a message to the patient, rather than an alert to a clinician, to remind the patient to take the medication if the input answer is negative. After a period of time, such as twenty-four hours, the processor of the monitoring device may then further evaluate the breathing patterns of the patient to see if the pattern recurs or has been resolved (by taking of the diuretics). An alert message would not be generated if the processor does not detect the previously detected respiratory pattern that triggered the initial query. Optionally, the processor may also confirm by a supplemental query that the patient has taken the medication. In such cases, monitoring may resume as usual thereafter. If, however, the recurring pattern is still or again detected by the processor after the initial query, a subsequent query, such as one with different questions, may be presented to the patient on the display device 116. After the predetermined number and frequency of queries have been performed, and the pattern is still detected by the processor, the monitoring apparatus may then trigger an alert message to notify the clinician of an imminent clinical event. In this manner, the processor may be configured to dispose of simple cases of non-compliance (such as dietary or exercise) or explain apparatus malfunctions due to, for example, unintentional disconnections or power loss, without the need for a clinical alert message requesting that the patient be contacted.

In one example, the controller or processor may access a memory that includes a set of queries. Each question of a query may be associated with one or more detectable respiratory patterns or events. A question may be broad (e.g., "has patient complied with the prescribed diet?") or specific (e.g., "has patient diet been fortified with potassium?"). With the set of questions indexed by such detectable patterns or events, the processor may then select a subset of questions for a query based on the detected pattern or event.

Questions may be presented in series in response to a particular monitoring session. For example, the controller may prompt two, three, four, five, six or more questions in a row so as to identify or rule out causes of the detected respiratory abnormality of the monitoring session that would or would not need an alert message. Alternatively, the processor may access an associated rank or priority for the question that represents an order of likelihood. Thus, the processor may conditionally present a series of questions according to the rank associated with each question. For example, the controller may present a first query. If in answering the first query, the patient response(s) indicates that the detected event does not (at least yet) require an alert, the response and determination may be logged and the processor may proceed to a second monitoring session during a predetermined period of time. If the respiratory pattern is again detected, a second query of a different rank from the first query may then be triggered. This detection and querying cycle may be repeated until no further queries remain or a response to a query indicates a need for an alert, after which the processor may then trigger an alert message.

Figure 2:
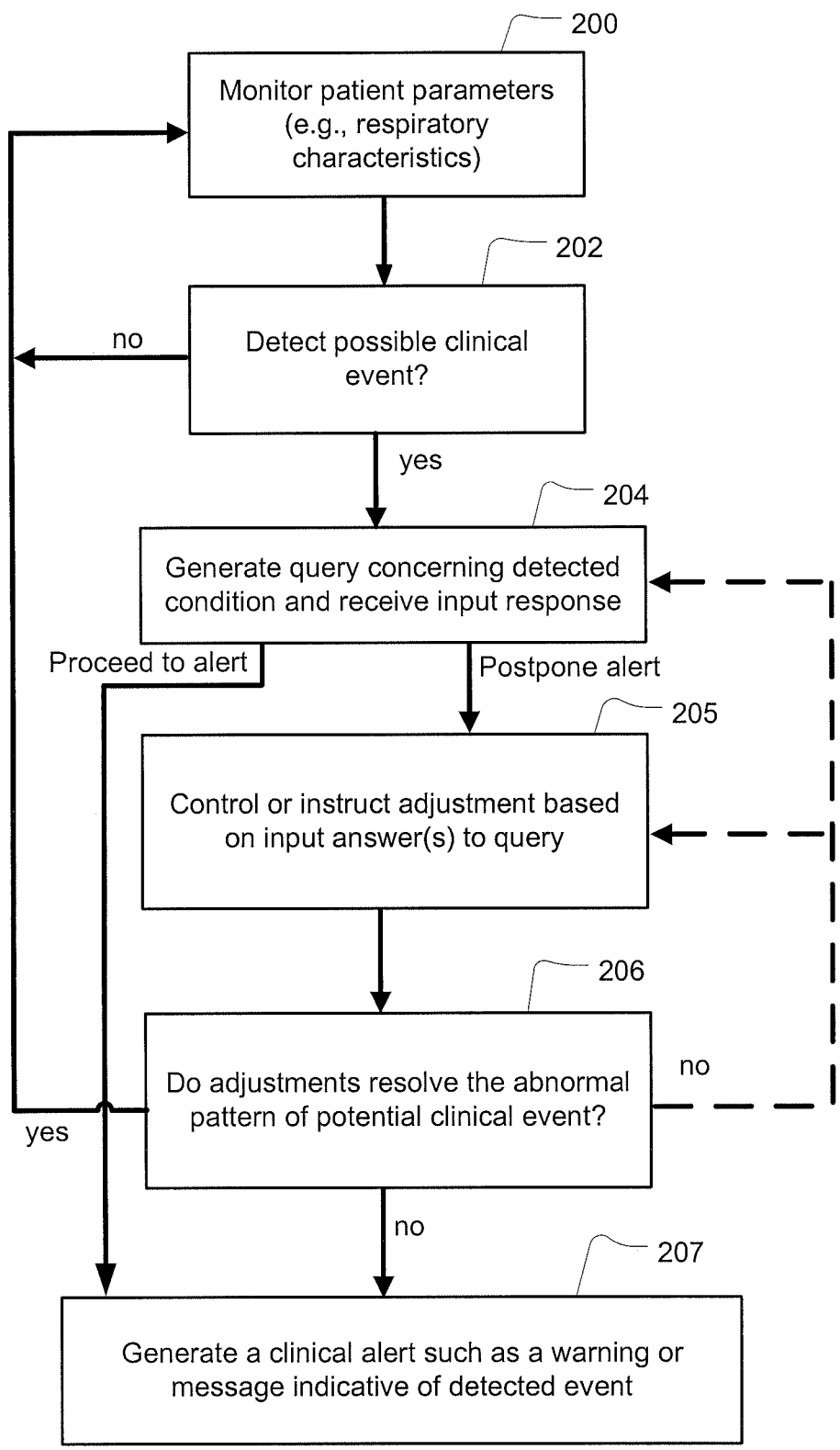
FIG. 2 is an example methodology for a monitoring apparatus that generates a clinical alert based on a set of queries that are triggered in response to detecting one or more respiratory patterns or events.

Another example methodology of the controller 104 of the monitoring apparatus 100 is illustrated in the flow chart of FIG. 2. At 200, the monitoring apparatus 100 may monitor respiration parameters of a patient. During this monitoring process, at 202, the monitoring apparatus 100 may detect a respiratory or breathing pattern indicative of the possibility of a clinical event that may require an alert message to a physician (e.g., dyspnoea events and/or other breathing irregularities or changes in the number or severity thereof). If no issue is detected at 202, the apparatus may continue monitoring at 200. If a potential alert condition is detected at 202, the controller at 204 may then trigger generation of one or more queries to evaluate a potential cause of the respiratory pattern and display them on display device 116 as discussed in more detail herein. Depending on the patient input response to the query, control may proceed to 207 to generate an alert message or postpone the alert by proceeding to 205.

At 205, the controller may optionally modify a control of a treatment in response to received answers to the patient queries (e.g., modify pressure treatment control parameters). For example, the controller may modify a target ventilation. Alternatively, the controller may maintain the same treatment as that provided in prior session during the detection of the respiratory pattern. Optionally, the apparatus may issue an instructional message to instruct the patient to make an adjustment, such as a change in diet or medication or a resetting or repair of the apparatus 100. At 206, the apparatus evaluates whether the adjustment of 205, was made and/or whether it resolved the previously detected issue of 202 (e.g., by determining if the detected pattern re-occurs or still exists). If the pattern has been resolved (e.g., the pattern is no longer detected), monitoring continues as usual at 200. If the respiratory pattern is still detected such as after a period of time (e.g., 24 to 48 hours later), the process may repeat at 204 or 205 if further queries or adjustments are available, and if not, a clinical alert is triggered at 207 as discussed in more detail herein.

Optionally, the clinical alert may include a warning or message taking a number of forms. For example, the controller, in response to a clinical alert, may activate a status light (e.g., an LED or an icon on a display screen or LCD) of the monitoring device. A more detailed message concerning the assessment of the indicator may also be displayed on the display screen. Optionally, the controller may also, or alternatively, send a message to a clinician or physician. Such a message may take the form of a wired or wireless communication. For example, the controller may generate a message via a paging system such as by automatically dialing a paging system. The controller may also be configured to generate an automated voice phone call message. The controller may also send the message by a fax transmission. In some embodiments, the controller may also send a message via any internet messaging protocol, such as an email message, or by any other internet data file transport protocol. The messages may even be encrypted to keep patient information confidential. A typical message may identify the patient. Such a message may also include the data of the changes recorded by the system of any other recorded patient information. Optionally, in some embodiments, the message may even express that the patient should be considered for additional RI or COPD treatment, hospitalization or an evaluation due to the detection of a potential exacerbation of RI or COPD.

While messages may be directed by the controller 104 to the patient via the display device 116 of the monitoring apparatus 100 and the physician via the communications device 120, in some embodiments, the messages could be directed more selectively. For example, the first message may be only transmitted to a physician or clinician by only transmitting the message to a physician system 122 through the communications device 120 without showing it on the display device 116. However, a second message, which may be a more urgent message, could then be actively displayed on the display device 116 in addition to transmitting it to the physician system 122. An audible alarm from an optional speaker controlled by the controller of the device may also be implemented. Use of an audible alarm may depend on the urgency of the message.

(2) Relapse Evaluation

In some embodiments, the monitoring apparatus may also be implemented with additional operations. For example, as previously mentioned, in may be useful to determine whether or not a hospitalized patient (e.g., a heart failure or COPD patient) is ready to be released or should not be released from the hospital. Releasing a patient too soon may not be beneficial for the patient, particularly if a relapse occurs shortly thereafter and the patient must be re-admitted. Heart failure and COPD patients suffer from decompensations and/or exacerbations and frequently require re-admission to a hospital due to relapse that might be avoided with a longer initial stay. Similarly, releasing a patient too soon may have other consequences. For example, hospitals may not be reimbursed or may only be partially reimbursed for the costs associated for a re-admission as a result of such a relapse. Thus, it would be useful to develop techniques for predicting the likelihood of relapse of a COPD patient so as to provide a tool for helping to avoid releasing of a patient from the hospital too soon. Some embodiments may be implemented to evaluate a patient's condition during a first time period to provide a predication relating to the potential for relapse in a subsequent time period. For example, for Heart failure and/or COPD patients, the potential for post-hospitalization decompensenations and/or exacerbations may be predicted from an evaluation of respiratory parameters during hospitalization, such as with an evaluation of the indicators and patterns previously identified.

Accordingly, a monitoring apparatus 100 may be configured to monitor respiratory parameters and may detect changes therein during a time period from admittance to discharge that may be indicative of a likelihood or post-discharge relapse. By monitoring the respiratory parameters and data within the time frame from admittance to a point near or prior to discharge, the apparatus may evaluate whether the patient might be at risk for re-admission soon after release. In this regard, the methodology of the monitoring device can provide a predictive warning to a physician to advise whether release might be too soon due to a risk of relapse. For example, it might warn that once released, the patient might be at a high risk for relapse and/or readmission and may further advise that careful monitoring for relapse should be considered for the particular patient or that the release should be reconsidered or postponed. In some cases, such a potential relapse indicator may be presented as a numerical value, such as an index or probability, which may provide an estimate within a range so as to yield a scaled indication of greater or lesser risk of future relapse.

Figure 3:
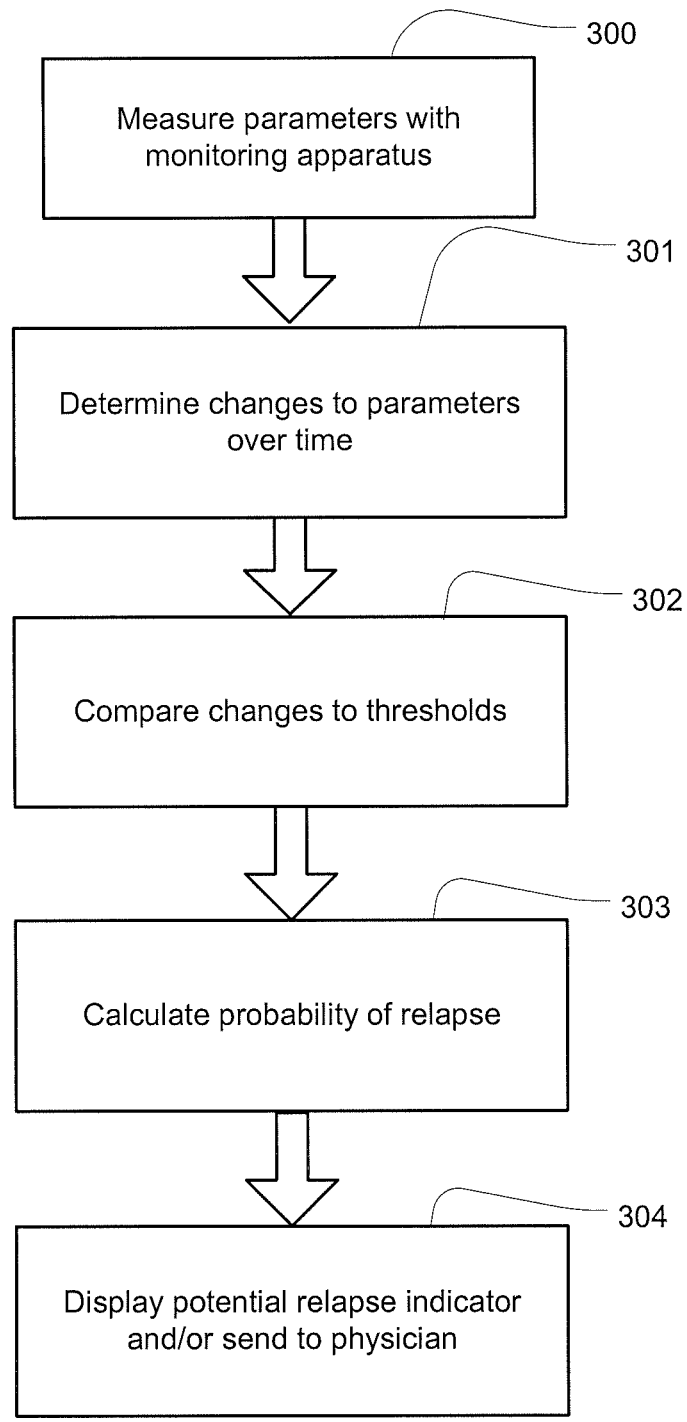
FIG. 3 illustrates a flow chart of an example patient relapse methodology suitable for implementation in some embodiments of the present technology.

FIG. 3 illustrates an example methodology for a monitoring apparatus that implements such a potential relapse detector, which may be used with a patient while the patient is hospitalized. As illustrated in FIG. 3, the monitoring apparatus methodology may detect a time series of parameters over the admission period, including one or more of the respiratory rate, minute ventilation, tidal volume, frequency of apneas, sleep-disordered breathing parameters (e.g., hypopneas, apneas), inspiratory waveform shape, expiratory waveform shape and the like with any one or more of the previously mentioned sensors, as illustrated at 300 of FIG. 3. These may be detected over a period of time of hospitalization. The apparatus may optionally perform an analysis of one or more of the detected respiratory parameters to assess how they have changed during the course of the hospitalization period at 301. Optionally, one or more of the parameters or the changes therein may be compared to one or more thresholds in order to evaluate a potential for relapse at step 302. Such thresholds may be empirically determined from historic data of one or more hospitalized patients who have relapsed and/or not relapsed after hospitalization. Optionally, such data may be based on thresholds taken from historic data of the particular patient. Optionally, a probability may be calculated based on a pattern of a plurality of the parameters or changes in a plurality of parameters at 303. Such comparisons and/or pattern evaluations may be made, for example, by a decision-tree, a classifier or any other method of evaluation. Based on the evaluation (e.g., comparison(s), pattern of changes, and/or probability), a message concerning potential relapse may be generated at 304. For example, data relevant to the likelihood of relapse, such as a potential relapse indicator or a calculated probability of potential relapse, may be displayed on display device 116 and/or sent to the physician or clinician.

In some embodiments, the potential relapse indicator or probability of potential relapse may be continuously updated and displayed based on a continuous detection of the parameters during the monitoring period of hospitalization. However, in some embodiments, the indicator, probability and/or message concerning the potential for relapse may be generated in response to a request made by a user, such as a physician or clinician, by accessing the apparatus through a user interface of the apparatus (e.g., one or more buttons or operation of a user interface of the apparatus) or by transmitting an electronic request to initiate the methodology in the apparatus. In this regard, the monitoring apparatus may be configured to generate the relapse prediction based on its previous detection of the parameters to be evaluated for the prediction. However, in some embodiments, the respiratory parameters used in the prediction methodology may be transmitted from the monitoring apparatus to another apparatus, such as a computer, which may implement the evaluation methodology that generates the relapse predication from the received parameters.

(3) Exercise Mode

In some embodiments, the monitoring apparatus 100, such as when implemented to provide a pressure treatment to patient suffering respiratory insufficiency, COPD or other similar ailments, may serve to enhance physical activity or mobility for a patient. For example, the apparatus may be implemented to provide non-invasive ventilation to provide respiratory support for patients during mobility. Such a non-invasive ventilation may enhance exercise capacity in COPD patients or emphysemic patients. Thus, in some embodiments, a pressure treatment methodology, such as a control algorithm for non-invasive pressure support ventilation, may be implemented to promote exercise or patient mobility with suitable pressure support modes.

As a COPD patient gradually exercises, their tidal volume and respiratory rate will increase. When the patient then rests, the tidal volume and respiratory rate decreases. In some embodiments of the present technology, a patient-responsive non-invasive ventilation methodology of the apparatus may be configured to adapt to patients' varying respiratory needs during exertion or exercise.

Figure 4:
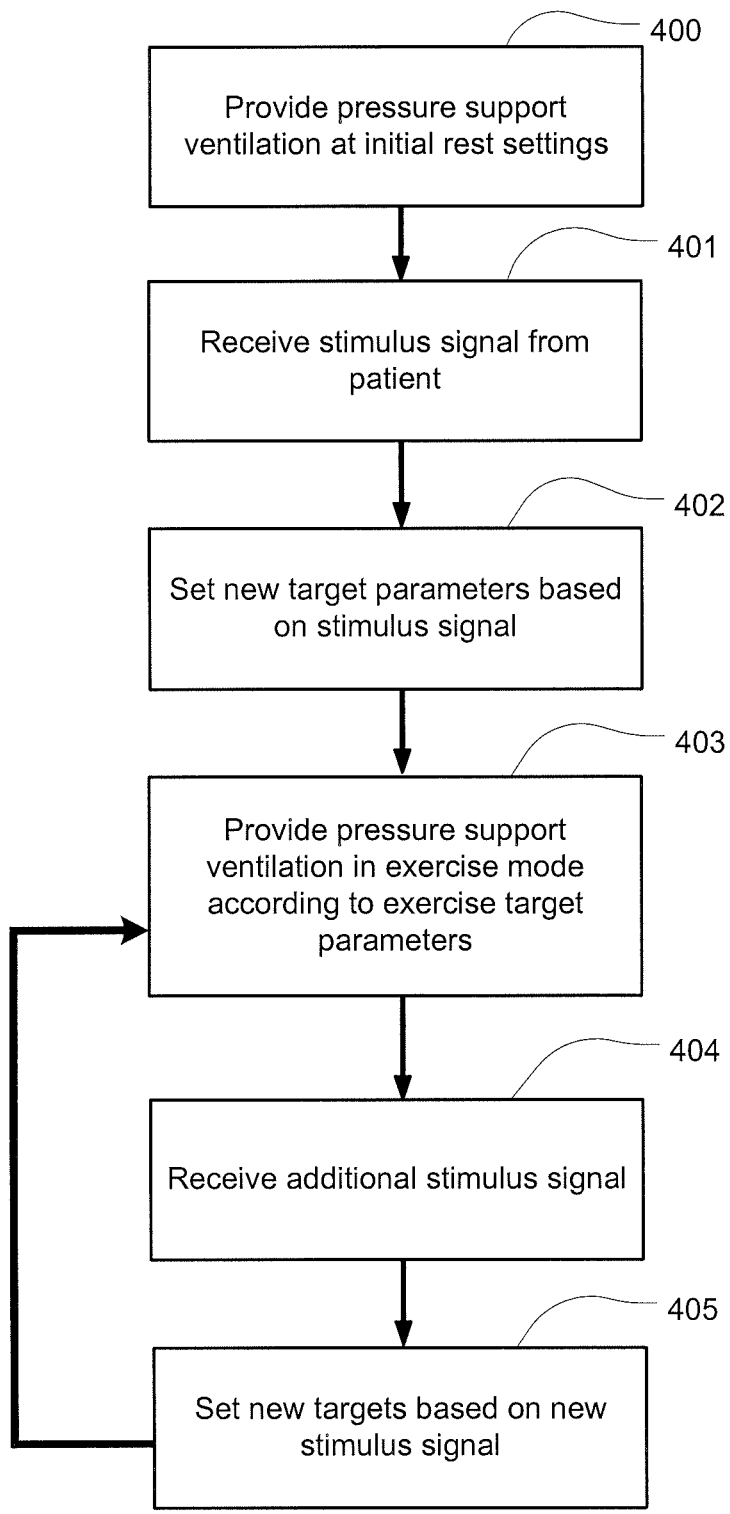
FIG. 4 is a further example flowchart for implementing control of treatment in some embodiments of the present technology.

Accordingly, FIG. 4 illustrates an example of a methodology of a controller for such an apparatus. During use, the controller will generally permit a change to pressure support control parameters, such as an increase in ventilation (e.g., tidal volume) and respiratory rate at levels, that are suitable for exercise or mobility up to a maximum ventilation, such as a minute ventilation, and/or maximum respiratory rate so as to provide pressure support at those levels. In order to achieve the desired levels, the apparatus may be configured to respond to a user or patient stimulus for setting the synchronization of the apparatus with the patient's exercise requirements.

For example, the apparatus may provide NIV at initial levels in a rest mode to provide a pressure support suitable for a patient at rest at 400. Thus, the apparatus may begin treatment by accessing stored values of target parameters for the rest mode where those values of the target parameters are suitable for controlling ventilation or pressure support for patient rest. The user or patient may then begin to exercise. During exercise or shortly before, the patient may then provide a stimulus, such as executing a trigger, to initiate a modification procedure of the apparatus so that the apparatus may begin an exercise mode at 401. The modification procedure permits the values of the target parameters of the pressure support to be modified or set such that the pressure support will be provided at more suitable levels (e.g., increases in target ventilation (e.g., minute ventilation or tidal volume) or in target respiratory rate, or in the maximum or minimum values suitable for controlling pressure support) for exercise at 402. Thus, the modification procedure of the exercise mode may allow enforcement of different minimum and/or maximum values and/or target values of respiratory control parameters in the exercise mode at 403 from the rest mode.

In some such embodiments, the triggered change or increase to the values of the control parameters of the pressure support ventilation for the exercise mode may optionally be predetermined. In such a case, the executed trigger may result in the apparatus accessing one or more stored values for the control parameters for the pressure support where the stored values of the control parameters are associated with the exercise mode. Such target, minimum and/or maximum values may be previously entered by a physician or clinician. For example, a respiratory rate target or ventilation target may be set as a physician selectable proportional function of the values of the control parameters of the rest mode so as to permit a proportional increase (or decrease) of the parameters from the rest mode. Optionally, in some embodiments, some of the values of the control parameters of the pressure support ventilation of the exercise mode may be learned so as to better synchronize with the level exercise of the user or patient. For example, the apparatus may learn the exercise respiratory rate, minute ventilation and/or tidal volume of the patient during an initial exercise period of the exercise mode or in response to a stimulus signal of the patient, such as by measuring these parameters from a flow signal in the initial period. Thereafter, such learned values may then be set for the control parameters of a later time period of the exercise mode.

In some embodiments, the stimulus for entering the exercise mode or making an adjustment to target values to accommodate the patient's state of exercise may be made by the patient by pressing a button of the treatment apparatus or a button on a remote control (e.g., a wired, wireless or infrared transmitter to transmit to an exercise mode signal or exercise synchronization signal to a receiver of the apparatus). Alternatively, the stimulus signal may be a detected physiological stimulus such as for example, a signal from a diaphragm electromyogram sensor, a signal from a vagal nerve sensor or an evaluation of a signal from a flow sensor.

In some embodiments, as further illustrated in FIG. 4, the apparatus may be configured to receive additional stimulus signals or executed triggers from the patient as the exercise progresses or cools down in or from the exercise mode. For example, with each additional stimulus signal, a new set of control values may be established. For example, at 404 a patient or user may trigger learning or loading of a further set of values for the control parameters. The new targets may then be set as the control parameters for the delivery of pressure support ventilation at 405. The apparatus 100 may then control the pressure support in accordance with the new settings at 403. Each set of control values may be higher or lower than the previous control values based on an increase or decrease of activity.

For example, in some embodiments, the exercise mode may have a predetermined time interval, such as a maximum time set by a physician or clinician. In some such embodiments, a timer may begin when the exercise mode starts and the mode may terminate when a preset maximum time is reached. During the exercise mode, the apparatus may deliver pressure support ventilation with the exercise mode control values that are suitable for patient exercise. At the conclusion of the exercise mode, the apparatus may switch to the rest mode, so as to deliver pressure support ventilation with the rest mode control values that are suitable for patient rest. Optionally, the apparatus or remote control may include a button to terminate the exercise mode before the maximum time is reached.

Still further, in some embodiments, the termination of the exercise mode may initiate a cool down mode. During the cool down mode, the values of the control parameters may be varied over a selectable period of time. For example, the values may be ramped from the values of the target parameters of the exercise mode to the values of the target parameters of the rest mode. For example, the respiratory rate and/or ventilation targets may be automatically modified so as to ramp down or be gradually stepped down over a period of time to the rest mode values.

It will be understood that modifications of the embodiments of the present technology may be devised within the spirit and scope of this description. For example, while an integrated device is contemplated by the present technology, the methodology of the components of the devices may be shared across multiple components of a system. For example, a monitoring device, that may or may not be separate from a pressure support device, may simply measure the physiological data from the patient and transfer the data to another processing system. The second processing system may in turn analyze the data to assess the indicators of the present technology. The second processing system may also evaluate the indicators and generate messages as described herein, such as by sending one or more of the described messages, in electronic form for example, back to the patient monitoring device for display on the device to warn the patient. Other variations can be made without departing with the spirit and scope of the technology.

The invention claimed is:

1. An apparatus for evaluating sensor signals representative of respiratory characteristics, the apparatus comprising:
at least one sensor adapted to measure at least one respiratory parameter of a user;
a display;
a controller, coupled to the at least one sensor and the display, the controller being configured to (i) evaluate the at least one respiratory parameter, (ii) generate a presentation of at least one query on the display based on the evaluation of the at least one respiratory parameter, the at least one query being configured to prompt for an input to the controller; and (iii) generate an alert message based on a user response to the query that is input to the controller; and a flow generator configured to generate a flow of breathable gas at a pressure above atmospheric pressure to a patient interface, and wherein the controller is configured to control the flow generator, wherein the controller is further configured to modify a pressure control parameter of the flow generator based on the at least one query.

2. The apparatus of claim 1, wherein the controller comprises a memory including a data structure of questions, and each question of the data structure of questions is associated with a detectable condition of the at least one respiratory parameter.

3. The apparatus of claim 2, wherein a question of the data structure of questions addresses medication compliance.

4. The apparatus of claim 2, wherein a question of the data structure of questions addresses dietary compliance.

5. The apparatus of claim 2, wherein the controller is further configured to select a first question of the data structure of questions in response to a detected condition of the respiratory parameter, and based on an input response to the first question, continue to evaluate the at least one respiratory parameter in a subsequent monitoring session before generating a subsequent alert message.

6. The apparatus of claim 5, wherein the controller is further configured to generate the subsequent alert message following the subsequent monitoring session and the generation of the subsequent alert message is based on a user response to a second question of the data structure of questions presented by the controller.

7. The apparatus of claim 1, wherein the control parameter comprises a target ventilation.

8. The apparatus of claim 1 wherein the alert message comprises a warning presented on the display.

9. The apparatus of claim 1 further comprising a communications device, wherein the alert message comprises an electronic message transmitted from the communications device.

10. The apparatus of claim 1 wherein the evaluation of the at least one respiratory parameter comprises a detection of dyspnoea.

11. The apparatus of claim 1 wherein: the controller is configured to (i) perform an evaluation of the at least one respiratory parameter during one or more monitoring sessions and (ii) generate for display a potential relapse indicator based on the performed evaluation of the at least one respiratory parameter, the potential relapse indicator representing a prediction of future relapse; and (iii) display the potential relapse indicator on the display.

12. The apparatus of claim 11, wherein the performed evaluation of the at least one respiratory parameter comprises an evaluation of a detected respiratory rate.

13. The apparatus of claim 11, wherein the performed evaluation of the at least one respiratory parameter comprises an evaluation of sleep disordered breathing events.

14. The apparatus of claim 11, wherein the performed evaluation of the at least one respiratory parameter comprises an evaluation of a measure of ventilation.

15. The apparatus of claim 11 wherein the performed evaluation of the at least one respiratory parameter comprises an evaluation of a change in the at least one respiratory parameter over the one or more monitoring sessions.

16. The apparatus of claim 11 wherein the potential relapse indicator comprises a numerical value.

17. The apparatus of claim 11 wherein the potential relapse indicator comprises a calculated probability.

18. The apparatus of claim 17 wherein the generation of the potential relapse indicator comprises a comparison of changes in a plurality of respiratory parameters with a plurality of thresholds.

19. A method for an apparatus for evaluating sensor signals representative of respiratory characteristics, the method comprising:

evaluating at least one respiratory parameter of a user from a sensor signal with a controller;

generating with the controller a presentation of at least one query on a display based on the evaluation of the at least one respiratory parameter, the at least one query being configured to prompt for an input to the controller;

generating an alert message with the controller based on a user response to the query that is input to the controller;

generating, with the controller and a flow generator, a flow of breathable gas at a pressure above atmospheric pressure to a patient interface during the evaluating; and modifying a pressure control parameter for the flow of breathable gas based on the at least one query.

20. The method of claim 19, further comprising accessing in a memory, a data structure of questions, each question associated with a detectable condition of the at least one respiratory parameter.

21. The method of claim 20, wherein a question addresses medication compliance.

22. The method of claim 20, wherein a question addresses dietary compliance.

23. The method of claim 20, further comprising selecting with the controller a first question in response to a detected condition of the respiratory parameter, and based on an input response to the first question, continuing to evaluate the at least one respiratory parameter in a subsequent monitoring session before generating a subsequent alert message.

24. The method of claim 23, wherein the controller generates the alert message following the subsequent monitoring session and the generation of the subsequent alert message is based on a user response to a second question presented by the controller on the display.

25. The method of claim 19, wherein the control parameter comprises a target ventilation.

26. The method of claim 19 further comprising presenting the alert message on the display.

27. The method of claim 19 further comprising transmitting, with a communications device, the alert message as an electronic message to another apparatus.

28. The method of claim 19 wherein the evaluating of the at least one respiratory parameter comprises detecting dyspnoea.

29. The method of claim 19 further comprising:

performing an evaluation with the controller of the at least one respiratory parameter during one or more monitoring sessions; and generating with the controller a potential relapse indicator based on the performed evaluation of the at least one respiratory parameter, the potential relapse indicator representing a prediction of future relapse; and displaying the potential relapse indicator on the display.

30. The method of claim 29, wherein the performed evaluation of the at least one respiratory parameter comprises an evaluation of a detected respiratory rate.

31. The method of claim 29, wherein the performed evaluation of the at least one respiratory parameter comprises an evaluation of sleep disordered breathing events.

32. The method of claim 29, wherein the performed evaluation of the at least one respiratory parameter comprises an evaluation of a measure of ventilation.

33. The method of claim 29 wherein the performed evaluation of the at least one respiratory parameter comprises an evaluation of a change in the at least one respiratory parameter over the one or more monitoring sessions.

34. The method of claim 29 wherein the potential relapse indicator comprises a numerical value.

35. The method of claim 34 wherein the potential relapse indicator comprises a calculated probability.

36. The method of claim 35 wherein the generating of the potential relapse indicator comprises a comparison of changes in a plurality of respiratory parameters with a plurality of thresholds.

* * * * *